United States Patent [19]

Gianturco

[11] Patent Number: 4,580,568
[45] Date of Patent: Apr. 8, 1986

[54] PERCUTANEOUS ENDOVASCULAR STENT AND METHOD FOR INSERTION THEREOF

[75] Inventor: Cesare Gianturco, Champaign, Ill.

[73] Assignee: Cook, Incorporated, Bloomington, Ind.

[21] Appl. No.: 656,261

[22] Filed: Oct. 1, 1984

[51] Int. Cl.⁴ .......................................... A61M 29/00
[52] U.S. Cl. ................................. 128/345; 138/97; 604/96; 267/182
[58] Field of Search ............... 128/345, 341, 343, 1 R, 128/334 R; 138/97, 119; 604/93, 96, 102, 104–107; 267/180, 182

[56] References Cited

U.S. PATENT DOCUMENTS

| | | | |
|---|---|---|---|
| 3,334,629 | 8/1967 | Cohn | 128/325 |
| 3,540,431 | 11/1970 | Mobin-Uddin | 128/325 |
| 3,774,596 | 11/1973 | Cook | 128/345 |
| 3,811,449 | 5/1974 | Gravlee et al. | 128/343 |
| 3,868,956 | 3/1975 | Alfidi et al. | 128/345 |
| 4,141,364 | 2/1979 | Schultze | 604/96 |
| 4,407,271 | 10/1983 | Schiff | 604/104 |
| 4,425,908 | 1/1984 | Simon | 128/1 R |

FOREIGN PATENT DOCUMENTS 894257 12/1981 U.S.S.R. .............. 267/182

OTHER PUBLICATIONS

Charles T. Dotter, "Trans. . . . Tube Graft", 329–332, Investigative Radiology 9–1969.
Carlos T. Potter, "Trans . . . Stint Grafing", Technical Developments, 4–1983.
Andrew Cragg, "Nonsurgical . . . Nitind Wire", 261–263, Radiology, 4–1983.
Morris Simons, "Vena Cava . . . Memory Alloy", 89–94, Radiology, 10–1977.

*Primary Examiner*—Robert P. Swiatek
*Assistant Examiner*—John G. Weiss
*Attorney, Agent, or Firm*—Woodard, Weikart, Emhardt & Naughton

[57] ABSTRACT

An endovascular stent formed of stainless steel wire of 0.018 inches diameter and arranged in a closed zig-zag pattern. The stent is compressed into a reduced size shape of an outer diameter which is many times smaller than its expanded shape. The stent is positioned in a passageway in the vascular system by means of a sheath while the stent is retained in the compressed reduced size shape. A flat-ended catheter is used through the sheath to hold the stent in place in the passageway while the sheath is withdrawn from the passageway allowing the stent to expand in the passageway into its expanded shape to hold the passageway open and enlarged. Other possible applications of the stent are in the respiratory, biliary and urinary tracts to reinforce collapsing structures.

10 Claims, 10 Drawing Figures

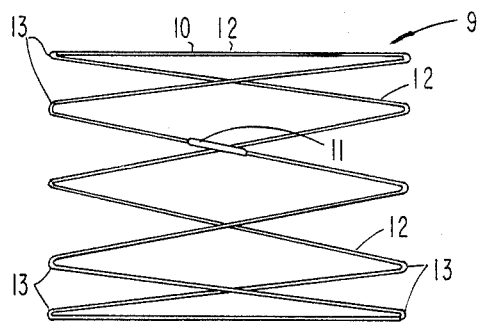 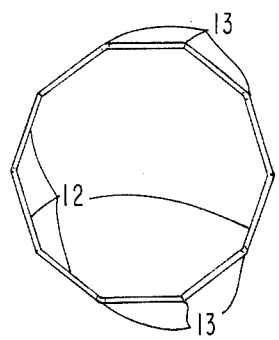
Fig.1 Fig.2
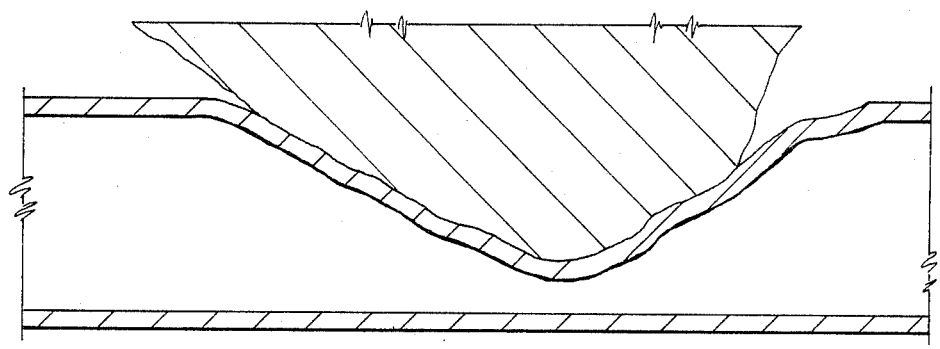
Fig.3
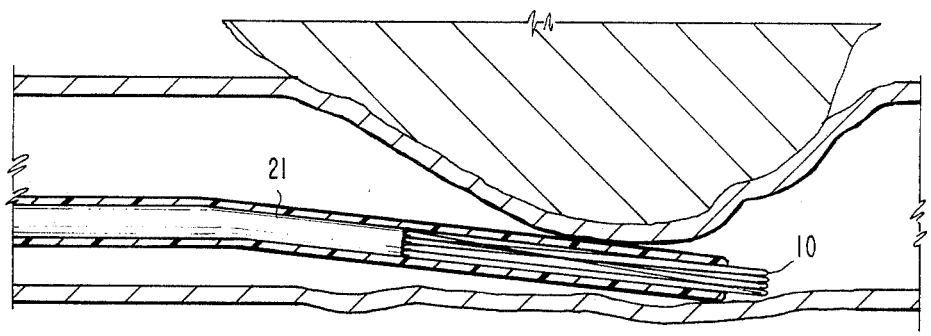
Fig.4
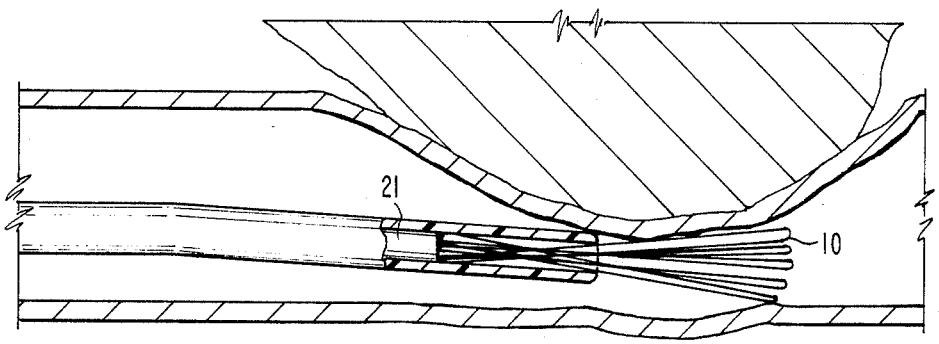
Fig.5

PERCUTANEOUS ENDOVASCULAR STENT AND METHOD FOR INSERTION THEREOF

BACKGROUND OF THE INVENTION

1. Field of the Invention

This invention relates to stents and a method for inserting a stent.

2. Brief Description of the Prior Art

It is desirable in various situations that means be provided for expanding a constricted vessel portion or for maintaining an open passageway through a vessel portion. Such situations arise, for example, in conjunction with the disease known as arteriosclerosis as well as the growth of a tumor so as to restrict or stop flow of blood through a blood vessel. Dr. Charles Dotter et al. reported in 1969 on the experimental use of coiled stainless steel wire stents placed in the popliteal arteries of dogs. Although the coils exhibited long-term patency, narrowing of the lumen occurred within them and only small coils could be passed percutaneously. See Dotter CT et al., *Transluminally-Placed Coilspring Endoarterial Tube Grafts,* Invest. Radiol., 1969; 4:329-332[1]. Recently, two laboratories reported on the use of a prosthesis constructed of a thermal shape memory alloy, nitinol, which is passed through a catheter. See Dotter CT et al., *Transluminal Expandable Nitinol Coil Stent Grafting,* Radiology, April, 1983; 147:259-260[2], and Cragg A. et al., *Nonsurgical Placement of Arterial Endoprostheses,* Radiology, April, 1983; 147:261-263[3]. Such stents can be complicated to use, requiring ice water or heated saline for placement. Also they have been found to produce luminal narrowing due to fibrin deposition on the stent wires.

Other references which may have relevance to the present invention are the following U.S. patents: Sakura U.S. Pat. No. 4,214,587; Alfidi U.S. Pat. No. 3,868,956; and Simon U.S. Pat. No. 4,425,908; and the Russian Pat. No. 978,821; also the following publications: C. Gianturco et al., *A new vena cava filter: experimental animal evaluation,* Radiology, December, 1980; 137:835-837[4]; and M. Simon et al., *A Vena Cava Filter Using Thermal Shape Memory Alloy,* Diagnostic Radiology, 125:89-94, October 1977[5]. Still another reference publication is D. Maass et al., *Radiology Follow-up of Transluminally Inserted Vascular Endoprostheses: An Experimental Study Using Expanding Sprials,* Radiology, September 1984; 152:659-663.

Objects of the invention are to provide a stent which is easy to place and use that reduces flow defects, luminal narrowing and occlusion.

SUMMARY OF THE INVENTION

One embodiment of the stent of the present invention might include a wire formed into a closed zig-zag configuration including an endless series of straight sections joined by bends. The stent is resiliently compressible into a smaller first shape wherein the straight sections are arranged side-by-side and closely adjacent one another for insertion into a passageway. The stent is resiliently expandable into a larger second shape wherein said straight sections press against the walls of the passageway to maintain it open.

One embodiment of the method of the present invention might involve inserting a stent by compressing a stent including a wire formed in a closed zig-zag configuration into a first shape wherein the zig-zag configuration includes side-by-side closely adjacent straight sections joined by bends with a stress therein. The compressed wire stent is then moved into a sheath. The sheath is then located with the distal end thereof in a passageway with the compressed wire within the distal end of the sheath. The sheath is then removed from the passageway while holding the stent in place, whereby the stress in the stent causes it to expand in the passageway to hold the passageway open and enlarged.

BRIEF DESCRIPTION OF THE DRAWINGS

FIG. 1 is a side elevation of a preferred embodiment of the present invention.

FIG. 2 is an end elevation of the structure of FIG. 1.

FIG. 3 is a section through a blood vessel showing a tumor reducing the size of the blood vessel.

FIG. 4 is a view similar to FIG. 3 showing one of the steps of the method of inserting the stent of the present invention.

FIGS. 5 and 6 are serial views showing further steps in the method illustrated in FIG. 4.

DESCRIPTION OF THE PREFERRED EMBODIMENT

Figure 6:
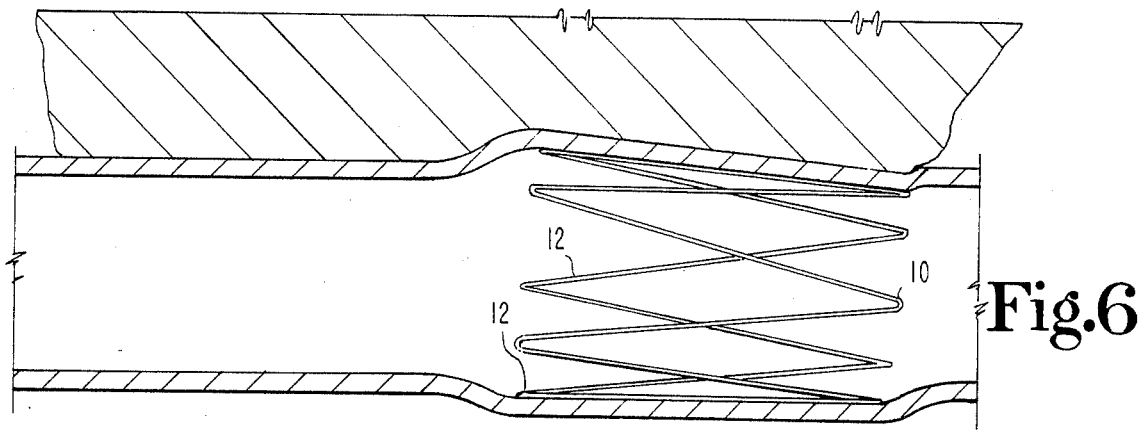

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to the drawings, there is illustrated in FIG. 1 a side elevation of a preferred embodiment of the stent 9 of the present invention which includes a length 10 of stainless steel wire formed in a closed zig-zag configuration. The wire is closed by a sleeve 11 which is welded to or tightly squeezed against the ends of the wire to produce the endless configuration. Referring to FIG. 4, the stent is shown in a resiliently compressed first shape wherein the straight sections 12 are arranged side-by-side and closely adjacent one another.

The straight sections 12 of the stent are joined by bends 13 which are relatively sharp. Thus, in one specific embodiment of the invention, the bends 13 are at a radius of no more than 0.2 cm. This specific embodiment of the invention includes wire 10 which is stainless steel of 0.018 inch O.D. The stent is resiliently expandable from the compressed first shape of FIG. 4 into a second shape illustrated in FIGS. 1, 2 and 6, wherein the straight sections 12 press against the walls of passageway to maintain the passageway open. FIG. 2 shows the end view of the stent in its expanded second shape. As illustrated in FIG. 2, the stent has generally a circular configuration or a cylindrical configuration when it is in its second expanded shape.

Figure 7:
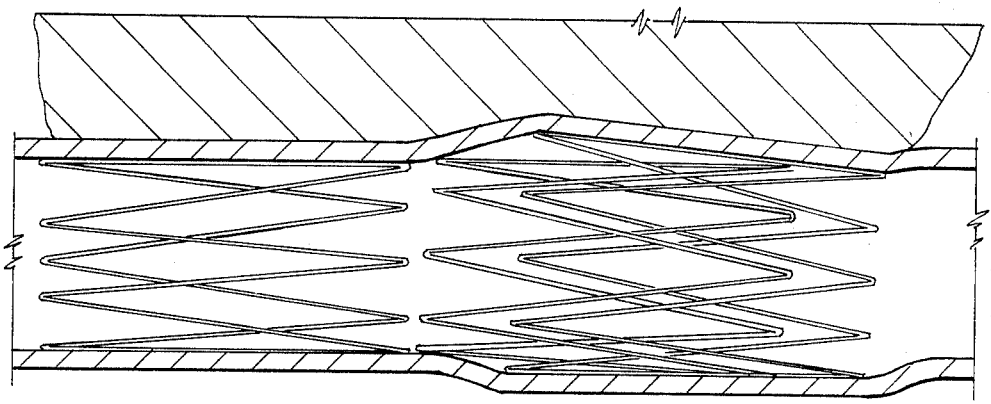
FIG. 7 is a view similar to FIG. 6 showing three stents having been placed in the blood vessel in accord with another embodiment of the invention.
Figure 8:
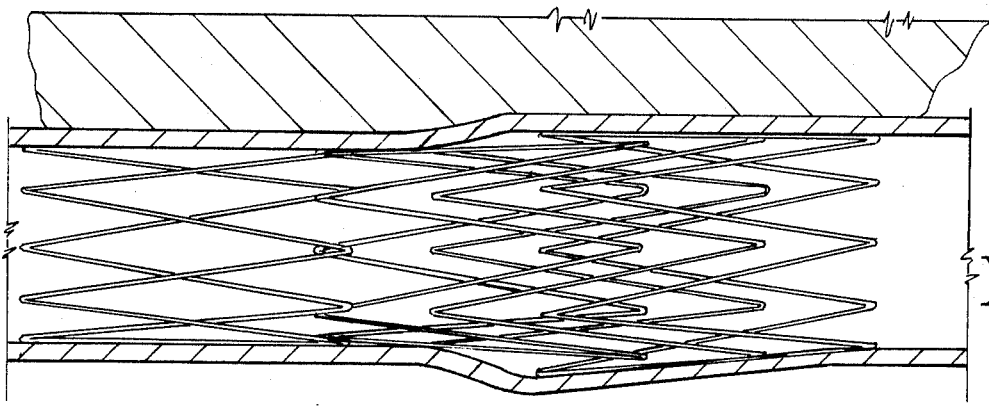
FIG. 8 is a view similar to FIGS. 6 and 7 showing four stents being placed in a blood vessel in overlapping fashion, in accordance with a further embodiment of the method of the present invention.
Figure 9:
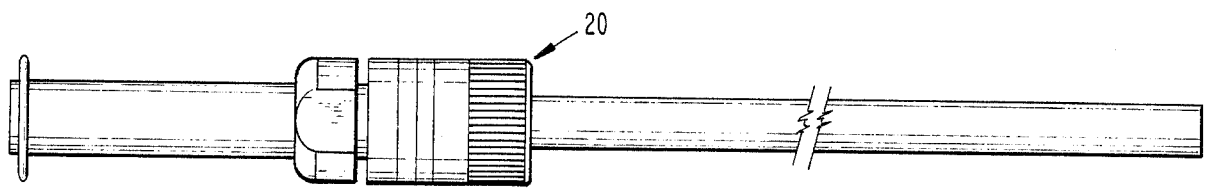
FIG. 9 is a side elevation of a sheath used in the method of the present invention.
Figure 10:
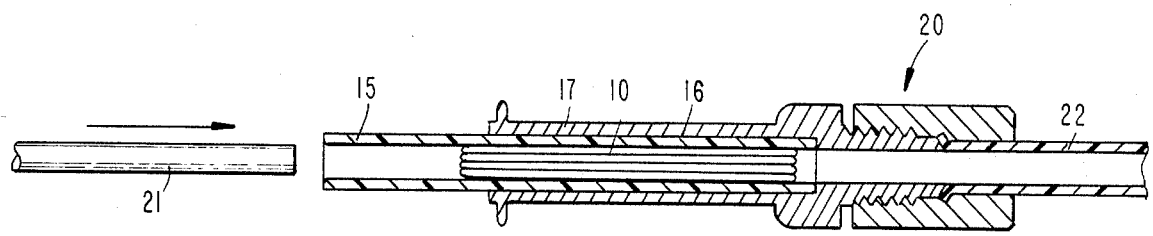
FIG. 10 is a sectional view of the proximal end of the sheath showing the stent being placed into the sheath as a part of the method of the present invention.

In order to practice the method of this invention, the stent is compressed into the first shape illustrated in FIG. 10 and is placed within a tubular cartridge 15 (FIG. 10). The cartridge 15 is inserted into the recess 16 in the adapter 17 of the sheath 20. The stent is then advanced through the sheath 20 by means of a flat-ended pusher 21. Thus in one specific embodiment of the invention, the flat-ended pusher was made of 8 French polyethylene tubing, although a flat-ended flexible metal rod is preferred. When the stent 10 reaches the end of the sheath as shown in FIG. 4, the flat-ended pusher is held while the sheath is withdrawn as shown in FIG. 5. This frees the stent, allowing it to expand and hug the vessel wall as shown in FIG. 6. If desired and if necessary for the particular situation, further stents can be added and can be placed in the blood vessel in the same fashion as above described. Thus in FIG. 7, an additional two stents are located one longitudinally of the first stent in the blood vessel and the other overlapping the first stent while in FIG. 8, four overlapping stents are used.

In tests of the invention, endovascular stents were designed and built in two sizes (5.5 cm long×4 cm diameter fully expanded; 3.0 cm long×2.5 cm diameter fully expanded) from stainless steel wire (0.018 in.) formed in a zig-zag pattern. They were placed for varying periods of time in the jugular vein, inferior vena cava and abdominal aorta of five dogs (See Table I below) and evaluated with regard to ease of use, dilating force, migration, patency, thrombogenicity, and local vascular changes.

Five adult, mongrel dogs (18–27 kg) were used in the study. They were anesthetized with i.v. sodium pentobarbital (Nembutal; 30 mg/kg) and the jugular vein, femoral vein, and femoral artery were surgically isolated. An incision was made in the vessels and a 8 French Teflon sheath containing an 8 French Teflon catheter with a taper-tip was inserted and under fluoroscopic monitoring advanced just beyond the area of interest. The stent was compressed and placed within a Teflon cartridge which fits inside the adaptor of the 8 French sheath. The 8 French catheter was removed, the cartridge was placed in the sheath adaptor, and the stent was advanced through the sheath with flat-ended 8 French polyethylene tubing. When the stent reached the end of the sheath, the polyethylene tubing was held while the sheath was withdrawn. This freed the stent allowing it to expand and hug the vessel wall. In certain cases, stents were placed one inside another and/or one after another (Table I). Following placement, angiograms were made immediately, after one week, and then at monthly intervals to document stent position and vascular anatomy. The dogs were euthanized at the end of the study by exsanguination under deep Nembutal anesthesia, and a complete necropsy was performed.

TABLE I

Summary of vascular stent placement in five dogs.

| Dog # (Wt) | Stent Size (Number Used) | Vascular Placement | Duration |
|---|---|---|---|
| 416 | 5.5 cm (5) | Two placed one inside the other in abdominal aorta (AA) bridging the celiac, cranial mesenteric, and right renal arteries | 1 month |
| | | Two placed one inside the other in superior vena cava (SVC) at level of right atrium | |
| | | One placed in the inferior vena cava (IVC) bridging both renal veins | |
| | 3.0 (3) | One placed in right jugular 8 cm above SVC, and two placed one inside the other in left jugular 8 cm above SVC | |
| 355 | 5.5 | One placed in AA bridging the celiac, cranial mesenteric, and right renal arteries | 3 months |
| | | Two placed one inside the other in IVC bridging both renal veins | |
| | 3.0 (3) | Two placed one inside the other in SVC at level of right atrium, and one placed 2.3 cm above the right atrium | |
| 354 | 5.5 (2) | One placed in AA bridging the cranial mesenteric and both renal arteries | 4 months |
| | | One placed in IVC bridging both renal veins | |
| 505 | 5.5 (5) | Four placed one after another in AA beginning at diaphragm (T11) and ending at L5 | 5 months |
| | | One placed in IVC at level of diaphragm | |
| | 3.0 (3) | One placed inside last long stent in AA at level of L4–L5 | |
| | | Two placed one after another in IVC between the hepatic and renal veins | |

No difficulties were encountered in the placement of the endovascular stents. They were easy to use and could be placed one inside another and/or one after another. The expansile strength of the stents was found to be dependent on stent length, diameter of stent wires, the number of folds in the wire of each stent, and the number of stents placed one inside another. Specifically, expansile force increased with decreased length, increased stent wire diameter, increased number of wire folds, and increased number of stents used.

Angiograms made of the stented vessels showed no flow defects, luminal narrowing, or occlusion. Blood vessels bridged by the stents remained patent and showed no indication of narrowing even after six months. No migration was noted with 29 of the 30 stents placed. One long stent (5.5 cm) placed alone in the inferior vena cava migrated approximately 2 cm cranially during the first week following placement, but no further movement occurred and no complications were encountered because of this migration.

Postmortem examinations showed the endothelial proliferation occurred around the stents where the wires contacted the vessel wall. By four weeks following placement, venous stents were almost completely (80%) covered by cell growth while aortic stents were just beginning (30%) to be incorporated. By 12 weeks, all stents were covered witth endothelium where the wires contacted the vessel wall. No growth was noted on wire segments that bridged side branches even after 6 months. In addition, no erosion of the vascular walls was noted, and no clot formation was seen on any of the stents.

Percutaneous expandable endovascular stents can be made of various diameters and lengths from stainless steel wire formed in a zig-zag pattern. They are easy to place percutaneously in veins and arteries and do not require the use of ice water or hot saline as do nitinol coils (2, 3). The dilating force of the stent can be controlled by manipulation of wire size, number of wire folds, and stent length. Expansion force increases with larger wire, but so does the size of the collapsed stent which necessitates use of a larger sheath for placement. Increasing the number of wire folds and decreasing the stent length also increase the dilating force. Therefore, stainless steel vascular stents can be tailor-made with regard to length, diameter, and expansion force.

Multiple stents can be employed depending on the circumstance. If the vessel of interest is longer than one stent, several stents can be placed one after another with slight overlap at the ends. In addition, if the expansion strength of one stent is not sufficient, several stents can be placed one inside another to increase the dilating force at a specific point.

Following placement in a blood vessel, the stent gradually becomes incorporated into the vascular wall by endothelial proliferation around the wires where they contacted the wall. This is similar to what has been noted in other studies where metal wire has been placed in the vascular system (2, 3, 4). Radiographic studies indicated that by one week after placement of the stent, sufficient endothelial proliferation had occurred to prevent migration, but during this first week, displacement was possible although not probable. After being in place for one month, the venous stents were approximately 80% encased by endothelium while the aortic stents were only about 30% encased. This difference is probably due to the greater flow and pressure in the aorta. By three months, all stent wires contacting the vessel wall were completely encased in endothelium. This incorporation into the vascular wall reduces thrombogenicity (3), but no clot was found even on the bare wires after 6 months. No cell growth was noted on any of the wire segments not in contact with the vascular wall, e.g., where stents bridged side branches. This observation corresponds with previous reports on the use of endovascular stainless steel wires (4). Therefore, the stents can bridge other vessels without occluding them or producing luminal narrowing at the branch points. This has not been reported for other types of endovascular stents (2, 3). Thus it appears that the stainless steel stents can be placed anywhere in the vascular system that will accomodate them. No luminal narrowing was noted in the stented vessels even after six months. This differs from the nitinol endovascular stents which have been shown to product luminal narrowing within 4 weeks due to fibrin deposition on the stent wires (1, 2, 3).

No clot formation was found on any of the stents at the time they were removed. This is similar to previously reported results (2, 3). No vascular erosion was seen probably because the vessels were normal and able to expand thus reducing the force of the stent wires against the vacular wall.

Results from this evaluation indicate that these stents should find various clinical applications. These may include re-establishment of flow in veins compressed by neighboring tumor (superior vena cava syndrome), maintenance of vascular patency after percutaneous balloon dilations, and correction of incomplete, long, irregular vascular stenosis. In addition, it may be possible to use these stents in other systems such as the respiratory, biliary, and urinary tracts to reinforce collapsing structures from extrinsic compression from neoplasma, maintain the dilatation of a balloon dilated segment of ureter, urethra, or bowel, aortic dissection, aortic aneurysm, and localization of a chronic puncture site.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A stent, comprising:
    a wire formed into a closed zig-zag configuration including:
    an endless series of straight sections;
    a plurality of bends;
    said straight sections joined by said bends to form the stent;
    wherein said stent is resiliently depressible into a smaller first shape wherein said straight sections are arranged side-by-side and closely adjacent one another for insertion into a passageway and said bends store stress therein; and,
    wherein said stent is resiliently expandable, by the release of the stress stored in said bends, into a second shape wherein said straight sections press against the wall of the passageway to maintain it open.

2. The structure of claim 1 additionally comprising a tubular cartridge having said stent therein, said stent being resiliently depressed into said smaller first shape.

3. The structure of claim 2 additionally comprising a sheath having a lumen therethrough, said sheath having an adapter recess arranged coaxially with said lumen and enlarged in size relative to said lumen, and a flexible member having a closed end and having an outer size sufficiently small to fit within said sheath yet sufficiently large to push said stent out of said sheath.

4. The stent of claim 1 wherein said wire is stainless steel of 0.018 inch O.D.

5. The stent of claim 4 wherein said stent in its second shape is 5.5. cm long and 4 cm in diameter.

6. The stent of claim 4 wherein said stent in its second shape is 3.0 cm long and 2.5 cm in diameter.

7. The stent of claim 4 wherein said bends are relatively sharp and are at a radius of no more than 0.2 cm.

8. A method for inserting a stent which comprises:
    compressing a stent including a resilient wire formed in a closed zig-zag configuration into a first shape wherein the zig-zag configuration includes side-by-side closely adjacent straight sections joined by bends with a stress therein;
    moving said compressed wire stent into a sheath;
    locating the distal end of the sheath in a passageway with the compressed wire within the distal end of the sheath;
    removing the sheath from the passageway while holding the stent in place whereby the stress in the stent causes it to expand in the passageway to hold the passageway open and enlarged.

9. The method of claim 8 wherein more than one stent is put in the passageway by said compressing, moving, locating and removing steps, said more than one sheath being overlapping.

10. The method of claim 8 wherein more than one stent is put in the passageway by said compressing, moving, locating and removing steps, said more than one stent being spaced longitudinally of the passageway.

* * * * *